United States Patent
Gaynor

(10) Patent No.: US 12,115,327 B2
(45) Date of Patent: Oct. 15, 2024

(54) SENSOR DEVICE AND METHODS OF OPERATION FOR A CATHETER BASED TREATMENT OF MYOCARDIAL MICROVASCULAR OBSTRUCTION

(71) Applicant: Silicon Microstructures, Inc., Milpitas, CA (US)

(72) Inventor: Justin Gaynor, Mountain View, CA (US)

(73) Assignee: MEASUREMENT SPECIALTIES, INC., Hampton, VA (US)

( * ) Notice: Subject to any disclaimer, the term of this patent is extended or adjusted under 35 U.S.C. 154(b) by 728 days.

(21) Appl. No.: 16/791,291

(22) Filed: Feb. 14, 2020

(65) Prior Publication Data
US 2020/0282189 A1 Sep. 10, 2020

Related U.S. Application Data

(60) Provisional application No. 62/814,173, filed on Mar. 5, 2019.

(51) Int. Cl.
*A61M 25/10* (2013.01)
*A61B 5/00* (2006.01)
(Continued)

(52) U.S. Cl.
CPC ....... *A61M 25/104* (2013.01); *A61B 5/02055* (2013.01); *A61B 5/0215* (2013.01);
(Continued)

(58) Field of Classification Search
CPC ........ A61M 2025/0002; A61M 25/104; A61M 25/10; A61M 2025/0004;
(Continued)

(56) References Cited

U.S. PATENT DOCUMENTS

2005/0049451 A1* 3/2005 Schock ................ A61M 25/10
600/18
2009/0143640 A1* 6/2009 Saadat ............... A61B 1/00089
606/41
(Continued)

FOREIGN PATENT DOCUMENTS

JP 2019502522 A 1/2019
WO 00/76390 A2 12/2000
(Continued)

OTHER PUBLICATIONS

Extended European Search Report, European Application No. 20161087.0-1132, European Filing Date, Jun. 25, 2020.
(Continued)

*Primary Examiner* — Theodore J Stigell

(57) ABSTRACT

Sensor devices and methods of operating for use with catheter-based treatments of microcardial microvascular obstruction by infusion of fluids having protective agents into vasculature are provided herein. Such catheter devices can include a first lumen configured for advancement over a guidewire and for passage of fluid having protective agents after removal of the guidewire and a second lumen for inflation of an angioplasty balloon and can further include a temperature and/or pressure sensor mounted on the catheter body. Such catheter devices can further include use of a distal occlusive membrane between the angioplasty balloon and distal end to facilitate infusion into microvasculature. The occlusive membrane can be deployed by relative movement of concentric channels, thereby reducing the need for additional lumen while optimizing the size of the catheter device and lumens.

14 Claims, 4 Drawing Sheets

(51) Int. Cl.
*A61B 5/0205* (2006.01)
*A61B 5/0215* (2006.01)
*A61F 2/958* (2013.01)
*A61M 25/00* (2006.01)

(52) U.S. Cl.
CPC ............ *A61B 5/6852* (2013.01); *A61F 2/958* (2013.01); *A61M 2025/0002* (2013.01); *A61M 2025/0004* (2013.01); *A61M 2025/105* (2013.01); *A61M 2205/3344* (2013.01); *A61M 2205/52* (2013.01); *A61M 2230/50* (2013.01)

(58) Field of Classification Search
CPC ...... A61M 2205/3344; A61M 25/0082; A61M 2025/1015; A61M 2025/105; A61M 2025/1045; A61M 2025/1097; A61M 2205/52; A61M 2230/50; A61M 2205/3331; A61M 2205/3368; A61B 5/0215; A61B 5/02055; A61B 5/6852; A61F 2/958; A61F 2/011; A61F 2/658
USPC ................ 604/101.04, 101.05, 107
See application file for complete search history.

(56) References Cited

U.S. PATENT DOCUMENTS

| | | |
|---|---|---|
| 2010/0222738 A1* | 9/2010 | Kassab ................ A61B 5/6853 604/99.04 |
| 2011/0275880 A1 | 11/2011 | Ferren et al. |
| 2018/0280172 A1* | 10/2018 | Hoem ................. A61M 25/104 |
| 2019/0046760 A1 | 2/2019 | Schwartz et al. |
| 2019/0275248 A1 | 9/2019 | Schwartz et al. |

FOREIGN PATENT DOCUMENTS

| | | |
|---|---|---|
| WO | 2007/130564 A2 | 11/2007 |
| WO | 2017120229 A1 | 7/2017 |

OTHER PUBLICATIONS

First Office Action from the CNIPA dated Jun. 28, 2023 (with English translation thereof) corres. to Appln. No. 202010146175.9, 21 pp.
First Office Action from the JPO dated Aug. 29, 2023 (with English translation thereof) corres. to Appln. No. 2020034587, 14 pp.

* cited by examiner

SENSOR DEVICE AND METHODS OF OPERATION FOR A CATHETER BASED TREATMENT OF MYOCARDIAL MICROVASCULAR OBSTRUCTION

CROSS-REFERENCES TO RELATED APPLICATIONS

This application is a Non-Provisional of and claims the benefit of priority of U.S. Provisional Application No. 62/814,173 filed Mar. 5, 2019, which is incorporated by reference in its entirety.

FIELD OF THE INVENTION

This invention relates sensor devices and methods of operating sensor devices in the field of drug delivery catheters, in particular, catheters used for treatment of myocardial microvascular obstructions and methods of use.

BACKGROUND

Coronary heart disease (CHD) is the leading cause of death and disability worldwide. Over 10 million deaths worldwide resulted from CHD in 2016. The effects of CHD are usually attributable to the detrimental effects of acute myocardial ischemia-reperfusion injury caused by microvascular obstruction (MVO). MVO typically arises in patients with an acute myocardial infarction ("heart attack"), for whom the most effective therapeutic intervention is usually angioplasty and, if necessary, stenting to re-establish blood flow. It appears that it is this treatment itself that triggers MVO. MVO causes the injury or death of heart cells upon re-establishment of blood supply after a blockage in a coronary artery is removed. In brief, solving the acute problem of coronary blockage often initiates the chronic problem of myocardial cell death.

MVO is the best predictor of adverse outcomes after a heart attack. Although the process of myocardial reperfusion continues to improve, there is still no effective clinical therapy for preventing MVO and its attendant myocardial reperfusion injury. MVO is a complex phenomenon, first recognized in 1966. It manifests as sluggish coronary blood flow and a characteristic coronary flow velocity profile, and affects 30%-40% of PPCI patients in whom coronary blood flow after treatment appears normal. The presence of MVO is associated with a larger myocardial infarction size, a lower left ventricle ejection fraction and worse clinical outcomes. In severe cases of MVO in which there is significant damage to the endothelium, it can produce intramyocardial hemorrhage.

There has been limited progress in the medical treatment of MVO. The patient's own whole blood, Ringer's Lactate, and heparin, among other infusates, have all been shown to improve circulation in the myocardial microvasculature. However, as Schwartz et. al. describes in publications WO 2017/120229, U.S. Pat. No. 10,315,016; US2018/0280172; US2019/0046760; and US2019/0275248, there are physiological difficulties in providing cardioprotective agents to the myocardial microvasculature.

In the above-noted publications, Schwartz et. al. describes a means of injecting infusates at controlled pressure to maximize the volume of fluid uptake across the myocardium (hereafter the "Schwartz process"). The challenge is described as generating infusate uptake in clogged or otherwise compromised microvasculature, rather than having all the infusate migrating into patent microchannels, capillaries and vessels. To achieve this, blood flow from the primary feeder vessel is completely obstructed with a balloon. With no incoming fluid stream, the pressure in the microvasculature quickly drops to what is known as the "coronary wedge pressure," which is the backpressure exerted by the microvasculature in the absence of antegrade blood flow. In the absence of antegrade blood flow, drug uptake is not preferential to the patent microvasculature, but diffuses at approximately the same rate into both patent and damaged or clogged vessels, driven by the squeeze/release action of the heart muscle upon the elastic vessels. After a bolus of infusate is delivered and taken up, the balloon is deflated and natural heartbeat is restored. It may require several such inflation/infusate delivery/deflation cycles until the microvasculature is able to accept the higher pressures of myocardial reperfusion. This is described in more detail in the cited references (see, for example, U.S. Pat. No. 10,315,016).

Pressure just upstream of the microvasculature is the controlling property for this process, and Schwartz et. al. describes the use of one or more pressure sensors distal of the obstructing balloon but proximal to the microvasculature to monitor infusion and recovery. In some embodiments, the pressure sensor is mounted on a pressure-sensing guidewire that is housed in a dedicated lumen during the procedure. In other embodiments, the sensor or sensors are mounted on the body of the catheter itself, for example, as shown in U.S. Pat. No. 10,315,016.) There are three notable shortcomings of the cited references.

Two shortcomings arise in the descriptions of the pressure sensing technology. In the existing art, the pressure sensors are either indicated as free-floating devices attached to a catheter, or as sensors integrated into a pressure sensing guidewire. In the former case, no description of how such a sensor would communicate with the outside world is provided, and no drawings indicate how such a sensing technology could actually be achieved. In the latter case, U.S. Pat. No. 10,315,016 provides an implementation. Such pressure-sensing guidewires are commercially available, such as the PressureWire from Abbott or the Verrata from Philips Healthcare. The disadvantage in this case is the amount of space such a guidewire would consume in the tip of the device, which must remain very small to reach the distal end of coronary arteries. U.S. Patent Publication No. 2018/0280172 shows a more accurate rendition of this invention, with item 132 being the infusion lumen. However, given that the outer diameter of the entire catheter is ideally less than 1 mm, injecting infusate through the small channel 132, which is generally much less than 1 mm in diameter and up to three meters in length, is a genuine practical challenge. In a third shortcoming of the Schwartz process, reliance on a precision dosing system that relies on feedback from flow and pressure sensors in the infusion line to optimize the rate of drug delivery is overly complex and expensive.

Thus, in view of the above noted shortcomings, there is a need for improved pressure sensing technology to better achieve the objectives of the prior art, including that of Reflow, Osprey and Corflow.

BRIEF SUMMARY

In one aspect, the invention pertains to an improved sensor device and sensor control methods in which pressure sensor measurements are obtained during a catheter-based treatment so that desired infusion pressures are generated, typically by manipulation of the occlusion balloon, coupled with a safety valve to prevent infusates from retrograde flow. This approach can be accomplished with only a modest equipment change, in which the occlusion balloon inflation pressure is connected by a feedback loop to the pressure sensor located distal of the balloon. Additionally, this invention provides a simpler and less expensive method of controlling infusion rates while protecting the body from retrograde migration of the infusates.

In one aspect, the invention pertains to a pressure sensor suited or configured for use with a catheter configured for treatment of myocardial microvascular obstruction. In some embodiments, the sensor comprises a pressure sensing element; a holder configured to support the pressure sensing element at or near a distal end of the catheter; and an electrical connector that receives a signal from a signal detector of the pressure sensing element such that the signal corresponds to a pressure detected by the pressure sensing element. The pressure sensing element can be any suitable pressure sensing means, such as at least one deformable membrane and means for signal detection from the membrane. Examples of such sensor designs are described in the publications noted above. The electrical connection is electrically connected to the signal detection means and includes one or more contacts to which an electrical cable can be connected to facilitate control and communication with the pressure sensor. The electrical connection can be according to a known standard or can be suited or configured for the requirements of the catheter to which the sensor is mounted. Holder is suited or configured to attach to the catheter near or at a distal end of a working channel of the catheter. In some embodiments, the holder is shaped to attach to an outer surface of a rounded working channel. Holder is formed of any material suitable for supporting the pressure sensing element, such as silicone, polymeric material, metal or a combination of materials. In some embodiments, holder is a substrate of the pressure sensing element. In some embodiments, the holder is of a suitably small size and extends along only along one side of the working channel so as to maintain an open passage at the distal end of the working channel for injection of the therapeutic agent. The holder can be made of any rigid or semi-rigid materials. The holder can be a base or substrate that supports or partly encases the pressure sensing element so that the sensor element is exposed to the surrounding environment sufficiently to determine an accurate pressure thereof. In some embodiments, the holder is configured to fixedly couple the pressure sensor to a distal end of a catheter for pressure monitoring during treatment of myocardial microvascular obstruction. In some embodiments, the holder is substantially rigid such that the pressure sensing element is held in a substantially fixed position at the distal end of the working channel so as to obtain a pressure near where a fluid having a protective agent is dispensed.

In one aspect, pressure sensor is configured for operation in a fluid-filled vascular environment, such as the coronary artery. In some embodiments, the pressure sensor is configured to detect whether a systolic blood pressure drops below 90 mm Hg. In some embodiments, the pressure sensor is configured to detect at least a range of pressures between 50-200 mm Hg. In another aspect, the pressure sensor is of a size suitable for mounting on the distal end of a catheter sized for vascular delivery, such as through the coronary artery for treatment of myocardial microvascular obstruction. In yet another aspect, the pressure sensor has a cross-sectional width, which is perpendicular to the axis of the catheter when mounted thereon, that is 3 mm or less (e.g. 2 mm, 1 mm, 0.5 mm, or less). This facilitates detection of a pressure within the vascular without increasing the delivery profile of the working channel and without blocking the working channel of the catheter to allow uninhibited flow of fluid having protecting agents therethrough. In yet another aspect, the pressure sensor is also a temperature sensor.

Such a sensor device can be incorporated into a drug delivery catheter system, which can include a catheter having a working channel; an occlusion or sealing membrane; a balloon inflation lumen; a balloon; and a pressure sensor mounted close to the distal end of the working channel, two concentric channels to control the sealing membrane; and a pressure seal distal to the balloon. In some embodiments, the pressure seal is disposed between the two concentric channels that define the inflation lumen. In some embodiments, the distal pressures sensor is connected to an electrical cable extending from the sensor to a proximal end of the cather. The cable can extend through the working channel or outside of the channel, such as on an outer surface of the catheter. In some embodiments, the working channel is configured and sized to accommodate a guidewire while serving as a working channel for drug delivery. In some embodiments, a stent is disposed over the balloon. In some embodiments, the catheter includes a temperature sensor mounted close to the distal end of the working channel. In some embodiments, the pressure sensor is also a temperature sensor. In some embodiments, the catheter is configured such that a space between the two concentric channels that control the sealing membrane serves as a gas transmission space for controlling the inflation of the balloon. In some embodiments, the proximal end of the electrical cable connecting to a pressure sensor is electrically connected to signal-processing and power circuitry.

Such catheter devices can include a first lumen configured for advancement over a guidewire and for passage of a fluid having protective agents (e.g. heparin) after removal of the guidewire and a second lumen for inflation of an angioplasty balloon. The catheter device can further include a temperature and/or pressure sensor mounted on the catheter body and disposed at or near the distal end. Such catheter devices can further include use of a distal occlusive membrane between the angioplasty balloon and distal end that is deployed by relative movement of concentric channels, thereby reducing the need for additional lumen while optimizing the size of the catheter device and lumens. As used herein, the term "channel" refers to a conduit or sheath having an inner lumen or space within.

In another aspect, the invention pertains to a method of operating a pressure sensor for treatment of myocardial obstruction of a patient. The method can entail obtaining signals from the pressures sensor that corresponds to pressure measurements within the vasculature that are coordinated or in obtained in response to inputs corresponding to various steps of a treatment method. In some embodiments, the method includes steps of: obtaining a first signal from a pressure sensor disposed at or close to a distal end of a catheter that is disposed in a coronary artery and advanced beyond an ischemic lesion in response to a first input inflating a balloon of the catheter. The first signal corresponds to a first pressure after inflation of the balloon of the catheter to confirm complete blocking of the coronary artery. Next, the method can include steps of: obtaining a second signal from the pressure sensor in response to a second input that facilitates injecting of a therapeutic agent into the coronary artery between the balloon and the myocardium and obtaining a third signal from the pressure sensor during continued injecting of the therapeutic agent into the coronary artery between the balloon and the myocardium thereby facilitating injection of the therapeutic agent at a controlled pressure.

In some embodiments, the second input deploys a sealing member of the catheter across the coronary artery between the balloon and the tip of the catheter before injecting of the therapeutic agent into the coronary artery between the balloon and the myocardium. In some embodiments, the method further includes obtaining one or more additional signals from the pressures sensor based on an input injecting the therapeutic agent into the coronary artery between the balloon and the myocardium thereby facilitating injection of the therapeutic agent at a controlled pressure. In some embodiments, the one or more additional signals are obtained over time (e.g. set time intervals, in rapid succession) to allow pressure monitoring during injection of the therapeutic agent. In some embodiments, obtaining the third signal is based on an input adjusting a rate or pressure of injection of the therapeutic agent based on pressure determined from the second signal. In some embodiments, the steps of obtaining the first, second and third signals is done automatically with a controller communicatively coupled to the pressure sensor and the catheter. The inputs of the treatment steps can be received manually by the clinician into the controller and/or can be received from a program stored on a memory of the controller. In some embodiments, the method further includes obtaining a fourth signal from the pressure sensor based on an input deflating the balloon and restoring blood flow through the artery. In some embodiments, one or more method steps can be performed by a controller based on automatic or manual inputs by the clinician.

In another aspect, the invention pertains to an improved method of treating myocardial obstruction by operation of a pressure sensor at or near a distal end of a treatment catheter device. The method can include: first passing a guidewire from outside the body into a coronary artery and advancing it beyond an ischemic lesion; advancing a catheter, such as that described above, along the guidewire; withdrawing the guidewire; inflating the balloon to completely block the coronary artery; deploying the sealing membrane across the coronary artery between the balloon and the tip of the catheter; and injecting a bolus of therapeutic agent into a space between the balloon and the myocardium at a controlled pressure, as determined by the pressure sensor in the tip of the catheter, and deflating the balloon to re-establish blood flow through the coronary artery. In some embodimenets, the method includes determining the pressure with a pressure sensor disposed close to the distal end of the catheter. The rate or pressure of injection of injection of the therapeutic agent in response to the determined pressure, either manually by the clinician or automatically by a controller communicatively coupled to the pressure sensor.

In some embodiments, such methods includes steps of: advancing a catheter device along the guidewire through a first lumen extending between a proximal end and a distal end of the catheter device, the catheter having a sensor device at or near a distal end thereof; removing the guidewire; inflating a distal angioplasty balloon on the catheter device through a second lumen (and optionally a stent disposed thereon); and delivering protective agent delivery into the vasculature through the first lumen. In some embodiments, the methods further include: deploying a distal occlusion membrane disposed on the catheter device between the distal angioplasty balloon and the distal end, before delivering the protective agent to promote infusion of the protective agent into the microvasculature. The distal occlusion membrane can be deployed by relative movement of concentric channels disposed about the first lumen, the space between concentric channels defining the second lumen. The methods can further include: monitoring the deployment of the distal occlusion membrane and adjusting the membrane by manipulating the concentric channels. The methods can further include sensing temperature and/or pressure by a sensor mounted at or near the distal end of the elongate catheter body and controlling operation of the catheter device and delivery of the protectant based on an output from the sensor.

DESCRIPTION OF THE INVENTION

Figure 1:
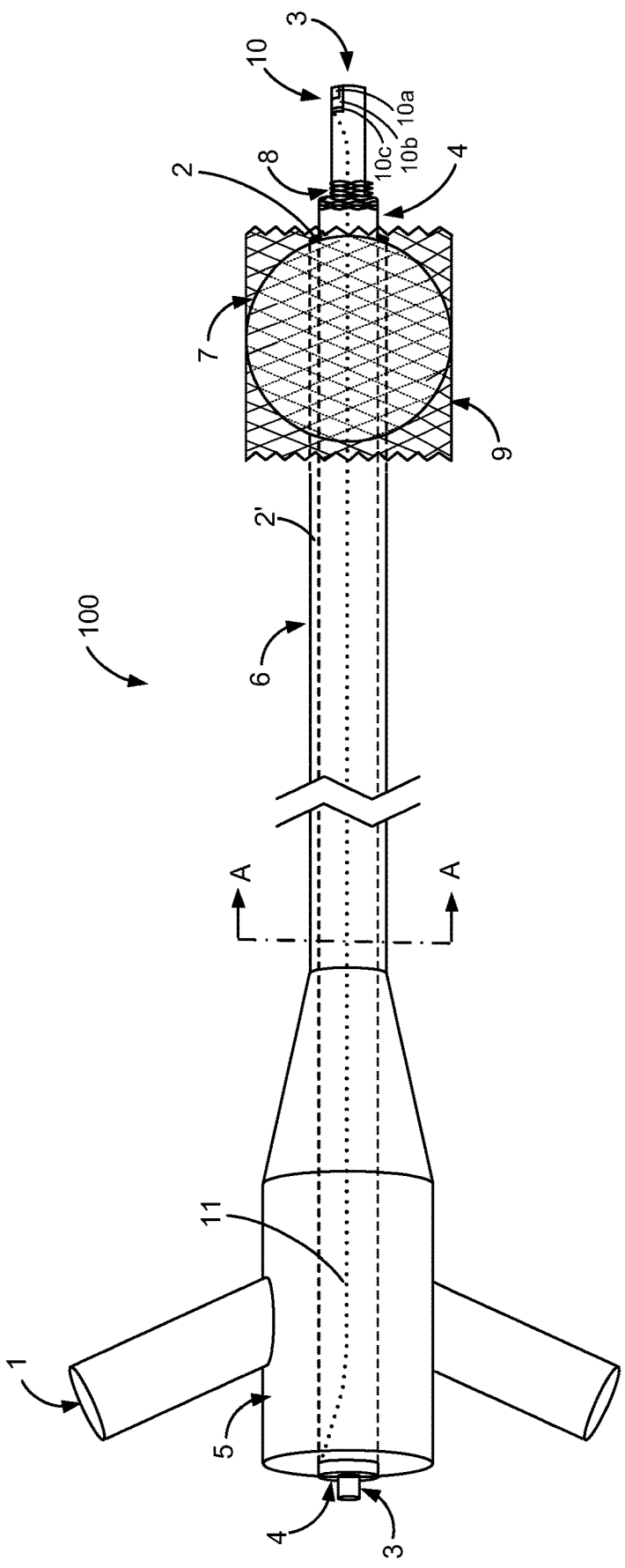
FIG. 1 shows an exemplary catheter device in accordance with some embodiments.

In a first aspect, the invention pertains to an improved sensor integrated within a catheter configuration that reduces the size of the catheter, improving its ability to reach the target area, while at the same time increasing the bore size through which the infusate is supplied, allowing a reduction in infusion pressure to achieve the same volume infusion. In another aspect, the invention utilizes a flexible pressure-sealing membrane to isolate the blood flow from the primary feeder vessel to the microvasculature. This maintains a pressure gradient down which the infusate flows, ensuring its delivery to the microvasculature.

Starting with the first aspect, some conventional catheters include three lumens, an inflation lumen, infusion lumen and Rx lumen, while other conventional catheters utilize four lumens. In some treatment methods using such catheters, the guidewire is first inserted through the coronary artery lesion and into the space between the lesion and the heart wall. Then, the guidewire is threaded into the infusion lumen and advanced to the end of the guidewire, at which time infusate is introduced into the anatomy distal to the stent balloon and/or occlusion balloon via the Rx lumen. In order to reach the affected vasculature, the entire catheter is of necessity quite small; commercial drug-infusing microcatheters are often one millimeter in diameter or less. Some conventional catheters utilize three or four lumens to accommodate one or two balloon inflation lines, the guidewire and infusion. It is thus clear that the infusion port in a four-lumen system would have to be quite small in diameter.

Although some conventional methods make use of a temperature and/or pressure sensing guidewire, with the sensors placed distal to the angioplasty and/or occlusion balloon, In one aspect of this invention, the catheter makes use of a pressure and/or temperature sensor mounted on or near the distal tip of the catheter, specifically adjacent the working channel where the fluid having protective agents is dispensed from, rather than in the guidewire. While some have suggested catheter-mounted sensors, the manner in which the sensors are attached, positioned and operated is not well described and is in need of further improvements. Such improvements are described further below.

In some embodiments, the method includes first steering a standard guidewire, without embedded sensors, to correct placement within the coronary feeder vessel. The catheter is guided into place after threading the guidewire onto the lumen. Then the guidewire is withdrawn, followed by inflating the angioplasty balloon (with or without a stent as required). While this balloon or the separate occlusion balloon is inflated, the cardioprotective agent is then introduced through the same lumen that accommodated the guidewire.

The advantages of this method are twofold. First, standard guidewires are both less expensive and, by reputation, easier to steer than pressure and temperature-sensing guidewires. Second, by using the method in which the guidewire is withdrawn before infusion, the need for an additional, specific infusion lumen is avoided, because the guidewire lumen can be used to inject the infusate after the guidewire has been withdrawn. Thus each of the lumens can be made larger, reducing the amount of pressure required to achieve a desired level of flow. The second aspect of the invention pertains to an improved catheter sensor configuration that allows a superior pressure profile to be achieved within the coronary artery during infusion.

The present invention further provides an alternative, less expensive means of controlling pressure in between the occlusion balloon and the myocardium. In some embodiments, the occlusion balloon described in the existing literature remains as a component in the invention described here, but can be supplemented with additional hardware to improve the safety and efficacy of the drug delivery system.

Some conventional catheters include a separate occlusion balloon in addition to the stent balloon. By implication, a separate balloon, with different properties than the stent balloon, is better suited to performing the desired occlusion than using the stent balloon for this purpose. In one aspect of the invention, this specific occlusion balloon is replaced with a filter membrane. Utilizing a membrane occlusion system provides marked benefits over a balloon occlusion system. Briefly, the flexible membrane, in contrast to the balloon, provides a flexing motion in response to arterial movement and thus maintains an advantageous pressure gradient between the delivery port of the catheter and the microvasculature to be served. This helps to force open the microvessels during diastole, improving uptake of the cardioprotective agent.

In another aspect, the pressure driving against the myocardium can be adjusted by adjusting the degree of occlusion by the occlusion balloon. In some embodiments, this can be accomplished either by an open-loop system in which the practitioner simply reads out the pressure from the pressure sensor on the distal end of the catheter or by a closed-loop system in which a targeted pressure is achieved by a balloon inflation controller that reads out the information from the pressure sensor.

FIG. 1 shows an exemplary catheter 100 that includes a working channel 3, which both accommodates a guidewire (not shown) as well as allowing infusion of a therapeutic fluid having cardioprotective agents distal of the occlusion membrane 8. The catheter can further include a balloon inflation lumen (e.g., a space 2' between channel 4 and channels 5, 6) in fluid communication with a balloon 7, and optionally a stent 9 over the balloon 7 (if necessary for a given procedure).

The catheter contains a distal pressure sensor 10 mounted close to the distal end of the working channel 3. The term "close" can be interpreted to mean within any of: 4" or less, 2" or less, 1" or less, 0.5" or less, 0.2" or less, or 0.1" or less.

Figure 2C:
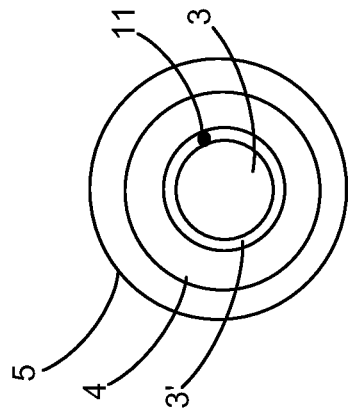
FIGS. 2A-2C shows detail cross-section view of exemplary catheter devices in accordance with some embodiments.
Figure 2B:
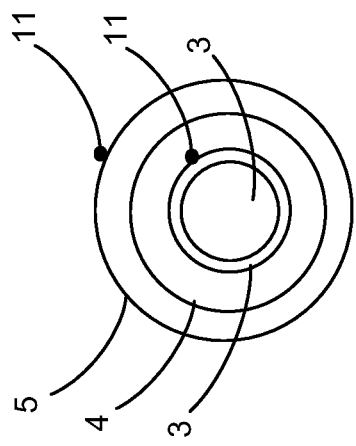
Figure 2A:
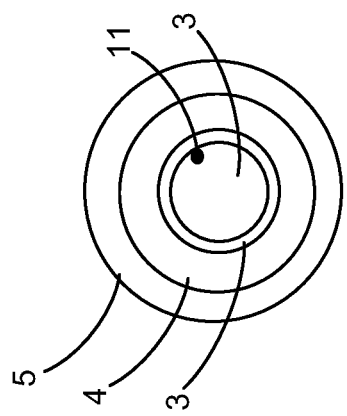

The pressure sensor 10 can be disposed just within the working channel, just outside of the working channel or precisely at the distal end. The pressure sensor 10 is powered and communicatively coupled through an electrical cable 11 that extends from the pressure sensor to a proximal end of the catheter. As can be seen in the cross-sections A-A shown in FIGS. 2A-2C, the electrical cable can extend within the working channel 3 (see FIG. 2A), can extend along the outer surface of the channel or catheter (both alternate positions shown in FIG. 2B), or can be embedded within a wall of a component of the catheter (see FIG. 2C). In some embodiments, the pressure sensor 10 can also be a temperature sensor. Control of the membrane 8 can be achieved using two concentric channels 3 and 4; in this case, the space between the channels 4 and channels 5,6 can serve as the inflation channel for balloon inflation. It is appreciated that the membrane can be deployed by any suitable approach. A pressure seal 2 distal to the balloon between 4 and 6 maintains the pressure in the balloon 7. It is appreciated that, in some embodiments, the pressure seal could be disposed elsewhere, such as within the balloon or proximal of the balloon, or any suitable location.

Pressure sensor 10 includes a pressure sensing element 10A that can include a pressure sensing means (e.g. deformable membrane) and a signal detector that detects variations in electrical signals from the pressure sensing means in response to changes in pressure. The pressure sensing element 10A is supported by holder 10B, which is suited or configured to be mounted to the catheter at or near the distal end of the working channel without increasing the delivery profile of the catheter and without inhibiting fluid flow through the working channel. In some embodiments, the holder 10B is rigid or semi-rigid so as to secure the pressure sensing element 10 adjacent the working channel during injection of the fluid having protective agents. In some embodiments, the holder 10B is specially shaped (e.g. curved, notched, angled) and/or configured to suspend the pressure sensing element 10A at or near the distal end opening of the working channel and inhibit lateral movement of the sensor from fluid flow during injection of the therapeutic agent. In some embodiments, holder 10B can be a substrate of the pressure sensing element. Pressure sensor 10 further includes an electrical connector 10C having electrical contacts that is electrically connected to the signal detection means of the pressure sensor 10 and can be connected to electrical cable 11 to facilitate control and communication of the pressure sensor 10 from a proximal end of the catheter, typically by a controller operably coupled to the catheter device.

Figure 4:
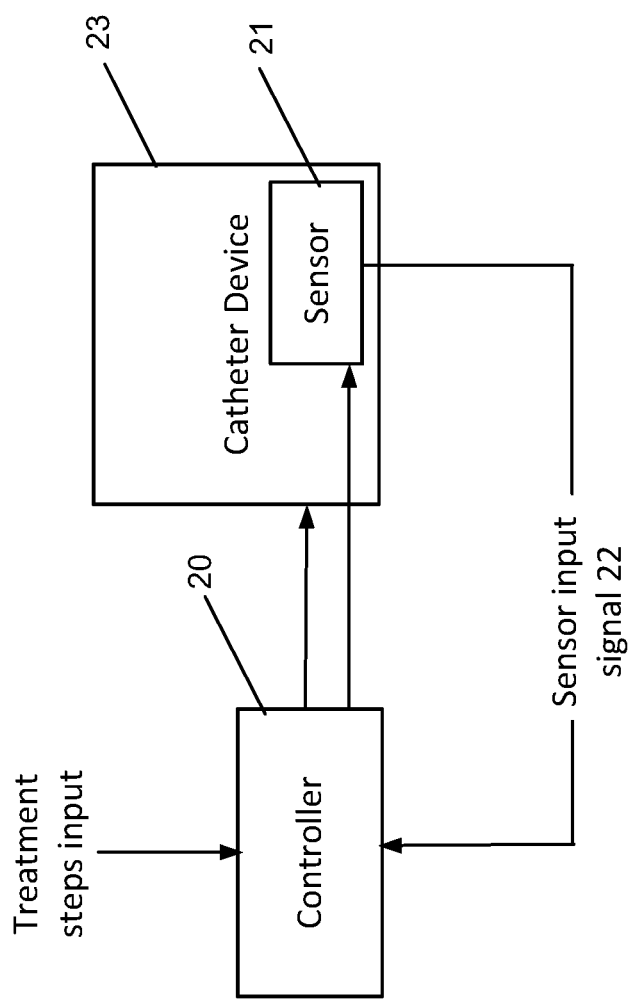
FIG. 4 shows a schematic of a catheter control system with pressure sensor in accordance with some embodiments.

FIG. 4 shows an exemplary system setup by which the sensor device 10 described above can be utilized in a catheter system to facilitate treatment of myocardial microvascular obstruction. Controller 20 is operably connected to a catheter device 23 and a sensor 21 incorporated into the catheter device 23, for example as described above. Controller 20 is configured to obtain sensor input signals 22 from the pressure sensor by which the controller operates the catheter device (e.g. inflation/deflation of balloon, deployment of a seal, adjustment of fluid injection, etc.). In some embodiments, controller 20 is configured to initiate injection of a therapeutic agent through the working channel of the catheter device 23 and adjust injection based on the pressure sensor input signals 22 obtained from the pressure sensor 21. In some embodiments, the injection utilizes sensor feedback to ensure an appropriate range of pressure is maintained during injection.

Figure 3:
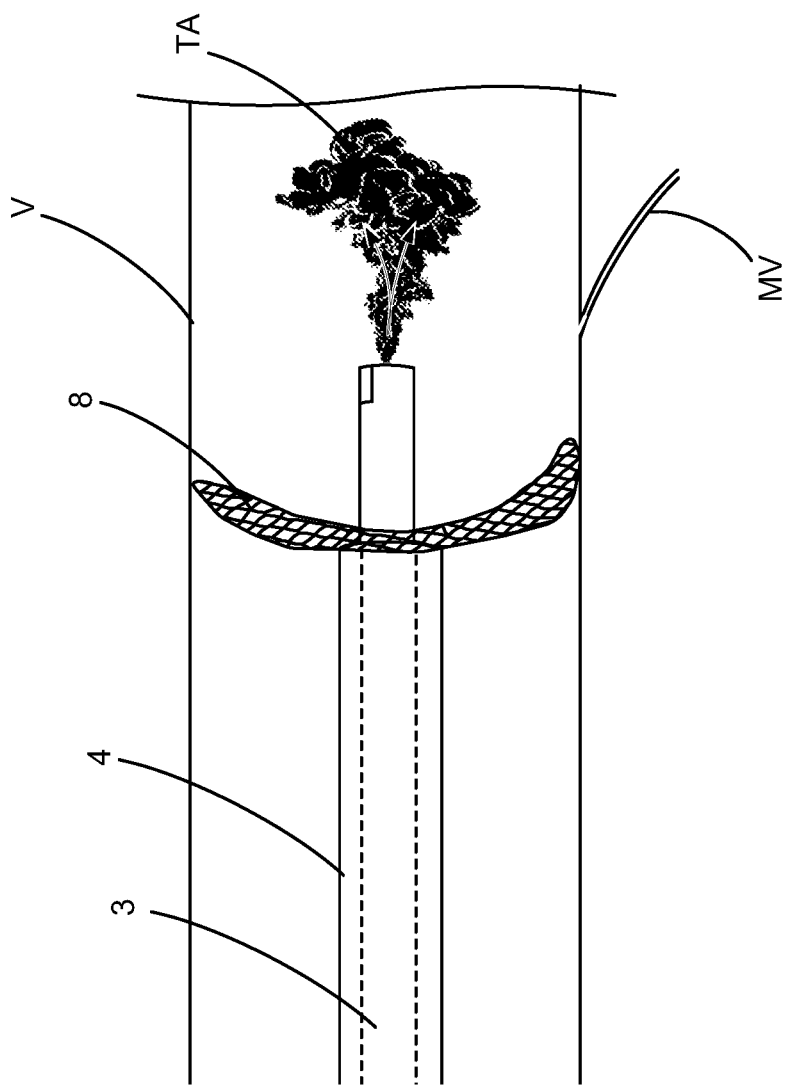
FIG. 3 shows a detail view of the occlusion membrane deployed in accordance with some embodiments.

The methods to use these device includes first steering a standard guidewire, without embedded sensors, to correct placement within the coronary feeder vessel. The catheter is guided into place after threading the guidewire onto the lumen 3. Then the guidewire is withdrawn, followed by inflating the angioplasty balloon 7 (with or without a stent 9 as required) through the inlet 1, which directs pressurized fluid via the space between channels 4 and 5 to the balloon 7. The membrane 8 is then manipulated via relative motion of channels 3 and 4 into its open, deployed configuration, as shown in FIG. 3, so as to contact the inside of the vasculature V. The balloon 7 is then deflated, allowing systolic pressure to reach the proximal side of membrane 8. The therapeutic agent TA having cardioprotective agents is then introduced through working channel 3. As the heart beats, the deformation of the deployed membrane 8 pushes the infusate towards the myocardium.

In the foregoing specification, the invention is described with reference to specific embodiments thereof, but those skilled in the art will recognize that the invention is not limited thereto. Various features, embodiments and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art. Each of the references cited herein are incorporated herein by reference for all purposes.

What is claimed is:

1. A treatment catheter for treatment of myocardial microvascular obstruction comprising:
   a working channel;
   an occlusion membrane;
   a balloon inflation lumen;
   a balloon;
   a pressure sensor mounted at or close to a distal end of the working channel;
   two concentric channels configured to control the occlusion membrane by relative movement of the two concentric channels, one of the two concentric channels being the working channel; and
   a pressure seal distal to the balloon.

2. The catheter of claim 1 wherein any of or combination of:
   the working channel is configured and sized to accommodate a guidewire and serve as a working channel for drug delivery;
   a stent is disposed over the balloon;
   the pressure sensor is also a temperature sensor; and
   a space between the two concentric channels that control the occlusion membrane serves as the balloon inflation lumen for controlling the inflation of the balloon.

3. The catheter of claim 1 further comprising:
   a controller operably coupled to the pressure sensor and operably coupled to the catheter, the controller having programmable instructions recorded on a memory thereof configured for controlling operation of the catheter based on a sensor output received from the pressure sensor.

4. The catheter of claim 1 further comprising:
   an electrical cable connected to the pressure sensor and extending to a proximal end of the catheter, wherein the electrical cable extends through the working channel or extends along an outer surface of the working channel.

5. The catheter of claim 1, wherein the pressure sensor comprises a pressure sensing element, and the pressure sensor further comprises:
   a holder configured to support the pressure sensing element, wherein the holder is configured to fixedly couple the pressure sensor to the distal end of the catheter suitable for treatment of myocardial microvascular obstruction; and
   an electrical connector that receives a signal from the pressure sensing element corresponding to a pressure detected by the pressure sensing element.

6. The catheter of claim 5, wherein the holder is substantially rigid such that the pressure sensing element is held in a substantially fixed position at the distal end of the catheter.

7. The catheter of claim 5, wherein the pressure sensor is configured for operation in a fluid-filled vascular environment.

8. The catheter of claim 5, wherein the pressure sensor is configured for detection of whether a systolic blood pressure drops below 90 mm Hg.

9. The catheter of claim 5, wherein the pressure sensor is configured to detect at least a range of pressures between 50-200 mm Hg.

10. The catheter of claim 5, wherein the pressure sensor is of a size suitable for mounting on the distal end of the catheter sized for vascular delivery through a coronary artery.

11. The catheter of claim 10, wherein the pressure sensor has a cross-section width perpendicular to the axis of the catheter when the pressure sensor is mounted thereon, wherein the width is 3 mm or less so as to facilitate detection of a pressure within the coronary artery without blocking the working channel of the catheter to allow inhibited flow of fluid having protective agents therethrough.

12. The catheter of claim 5, wherein the pressure sensor is also a temperature sensor.

13. The catheter of claim 1, wherein the pressure sensor is configured to be positioned within a delivery profile of the working channel.

14. A catheter device for delivering and infusing protective agent delivery into microvasculature, the device comprising:
   an elongate catheter body having a proximal end and a distal end;
   a first lumen extending between from a proximal opening to a distal opening, the proximal opening being at or near the proximal end and the distal opening being at or near the distal end, wherein the first lumen is configured for delivery of a guidewire and delivery of the protective agent after guidewire removal;
   a distal angioplasty balloon disposed on a distal portion of the elongate catheter body proximal of the distal end;
   a second lumen extending between the proximal end and the distal portion, the second lumen being communicatively coupled with the distal angioplasty balloon to facilitate inflation of the distal angioplasty balloon;
   a sensor mounted on the elongate catheter body and disposed at or along the distal portion of the elongate catheter body, the sensor is positioned within a delivery profile of the elongate catheter body;
   an electrical cable connected to the sensor and extending to the proximal end of the elongate catheter body, the electrical cable extends through the first lumen;

a control unit configured to control operation of the catheter device based on a sensor output received from the sensor;

an occlusion membrane; and two concentric channels configured to control the occlusion membrane by relative movement of the two concentric channels, one of the two concentric channels being the first lumen.

\* \* \* \* \*